(12) United States Patent
Campbell et al.

(10) Patent No.: US 11,116,947 B2
(45) Date of Patent: Sep. 14, 2021

(54) BALLOON SEAL STRESS REDUCTION AND RELATED SYSTEMS AND METHODS

(71) Applicant: W. L. Gore & Associates, Inc., Newark, DE (US)

(72) Inventors: Carey V. Campbell, Flagstaff, AZ (US); Seana Giardini, Flagstaff, AZ (US); James L. Goepfrich, Flagstaff, AZ (US); Matthew E. Maulding, Flagstaff, AZ (US); Benjamin M. Trapp, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 251 days.

(21) Appl. No.: 14/185,223

(22) Filed: Feb. 20, 2014

(65) Prior Publication Data

US 2014/0277065 A1    Sep. 18, 2014

Related U.S. Application Data

(60) Provisional application No. 61/799,638, filed on Mar. 15, 2013.

(51) Int. Cl.
*A61M 25/10* (2013.01)

(52) U.S. Cl.
CPC .... *A61M 25/1029* (2013.01); *A61M 25/1002* (2013.01); *A61M 2025/1031* (2013.01); *A61M 2025/1075* (2013.01); *A61M 2025/1084* (2013.01)

(58) Field of Classification Search
CPC .............. A61M 25/10; A61M 25/1002; A61M 25/1029; A61M 25/104; A61M 2025/1031; A61M 2025/1052; A61M 2025/1059; A61M 2025/1068; A61M 2025/1075; A61M 2025/1084; A61M 2025/1088; A61M 29/02; A61B 5/6853; A61B 17/12022; A61B 17/12136; A61B 2017/22048; A61B 2017/22051; A61B 2017/22065; A61B 2017/320048; A61B 2017/3486
USPC ......................................................... 606/192
See application file for complete search history.

(56) References Cited

U.S. PATENT DOCUMENTS

| | | | |
|---|---|---|---|
| 5,192,296 A | | 3/1993 | Bhate et al. |
| 5,470,313 A | * | 11/1995 | Crocker ............ A61M 25/1002 604/103.07 |
| 5,522,882 A | | 6/1996 | Gaterud et al. |
| 5,755,690 A | | 5/1998 | Saab |
| 5,843,116 A | | 12/1998 | Crocker et al. |

(Continued)

FOREIGN PATENT DOCUMENTS

| | | | |
|---|---|---|---|
| CN | 1274294 A | | 11/2000 |
| CN | 1473058 A | | 2/2004 |

(Continued)

OTHER PUBLICATIONS https://www.thefreedictionary.com/densified, definition of term "densified" retrieved Aug. 12, 2018.*

(Continued)

*Primary Examiner* — Wade Miles
*Assistant Examiner* — Kankindi Rwego

(57) ABSTRACT

The present disclosure is directed toward devices, systems and methods that reduce stress being exerted directly onto balloon seals.

17 Claims, 3 Drawing Sheets

(56) References Cited

U.S. PATENT DOCUMENTS

| | | | |
|---|---|---|---|
| 6,027,517 A | 2/2000 | Crocker et al. | |
| 6,120,523 A | 9/2000 | Crocker et al. | |
| 8,636,690 B2 | 1/2014 | Alpini et al. | |
| 9,402,983 B1* | 8/2016 | Nath | A61M 25/1002 |
| 2001/0012934 A1 | 8/2001 | Chandrasekaran | |
| 2003/0074016 A1* | 4/2003 | Campbell | A61F 2/958 |
| | | | 606/192 |
| 2004/0084304 A1 | 5/2004 | Thompson et al. | |
| 2006/0135980 A1* | 6/2006 | Trinidad | A61M 25/1002 |
| | | | 606/191 |
| 2008/0097301 A1* | 4/2008 | Alpini | A61M 25/1029 |
| | | | 604/103.07 |
| 2008/0125710 A1* | 5/2008 | Hobson | A61L 29/085 |
| | | | 604/103.01 |
| 2008/0125711 A1* | 5/2008 | Alpini | A61M 25/1002 |
| | | | 604/103.06 |
| 2008/0140173 A1* | 6/2008 | Eskaros | A61M 25/10 |
| | | | 623/1.11 |
| 2009/0283206 A1 | 11/2009 | Eskaros et al. | |
| 2010/0030144 A1 | 2/2010 | Brunner et al. | |
| 2010/0049123 A1* | 2/2010 | Alpini | A61M 25/0009 |
| | | | 604/103.06 |
| 2012/0109057 A1 | 5/2012 | Krolik et al. | |
| 2012/0277718 A1* | 11/2012 | Campbell | A61M 25/1018 |
| | | | 604/500 |
| 2012/0330232 A1 | 12/2012 | Hedberg et al. | |
| 2013/0018406 A1 | 1/2013 | Campbell et al. | |
| 2013/0253466 A1* | 9/2013 | Campbell | A61M 25/10 |
| | | | 604/500 |

FOREIGN PATENT DOCUMENTS

| | | |
|---|---|---|
| CN | 101822867 A | 9/2010 |
| EP | 0 897 730 A2 | 2/1999 |
| EP | 1 557 193 | 7/2005 |
| JP | 08-052219 A | 2/1996 |
| JP | 2000-509304 A | 7/2000 |
| JP | 2003-062078 A | 3/2003 |
| JP | 2005-230535 A | 9/2005 |
| JP | 2006-504848 A | 2/2006 |
| JP | 2010-500107 | 1/2010 |
| JP | 2010-500108 A | 1/2010 |
| JP | 2010-500113 A | 1/2010 |
| JP | 2011-206124 A | 10/2011 |
| WO | WO-97/40877 A1 | 11/1997 |
| WO | 2004/041529 A1 | 5/2004 |
| WO | 2008/021020 A2 | 2/2008 |
| WO | 2008/021006 A3 | 8/2008 |
| WO | 2010/079494 | 7/2010 |

OTHER PUBLICATIONS

International Search Report and Written Opinion for PCT/US2014/17653 dated Jun. 26, 2014, corresponding to U.S. Appl. No. 14/185,223, 6 pages.

* cited by examiner

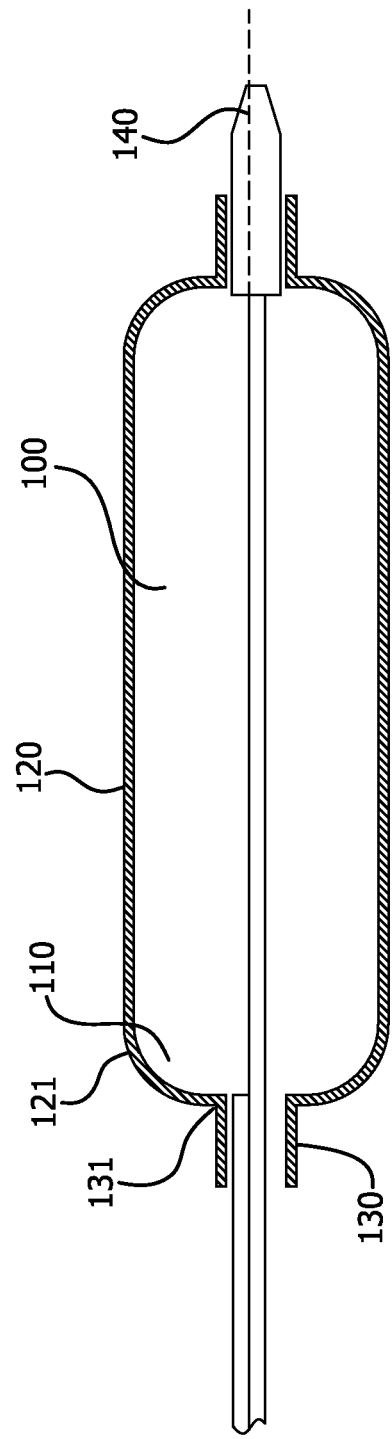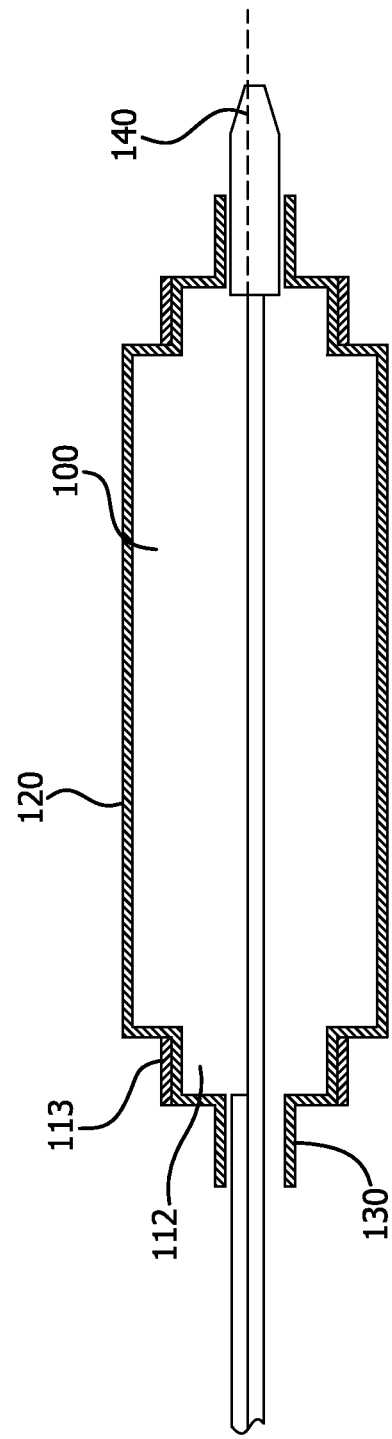

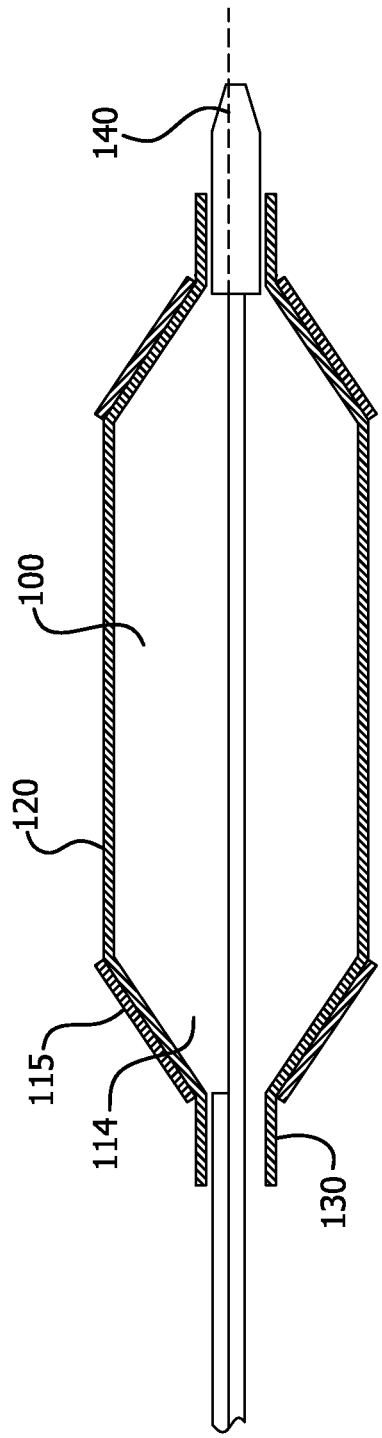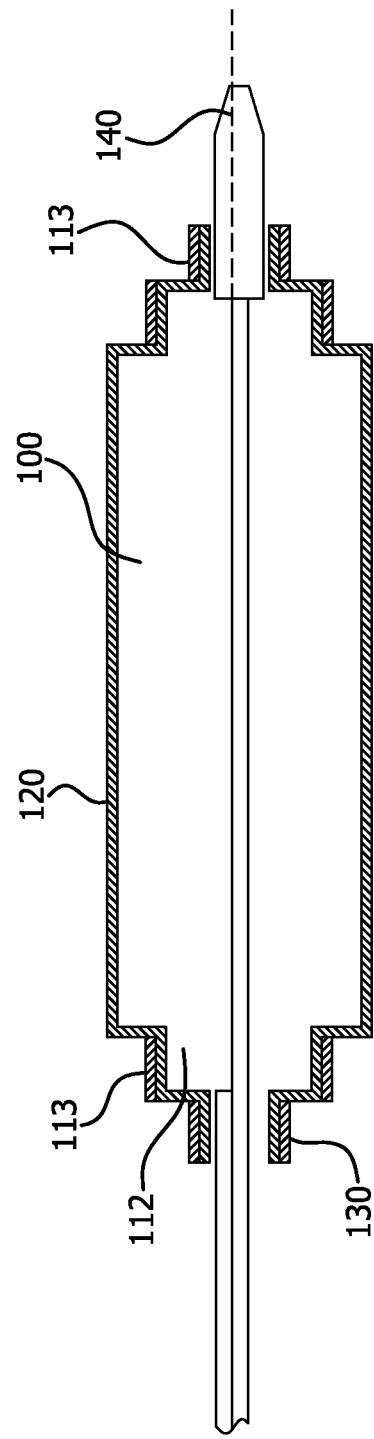

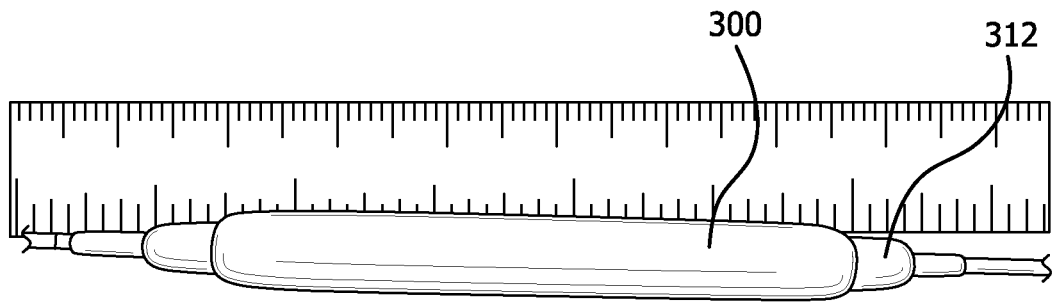
FIG. 3A  14 atm
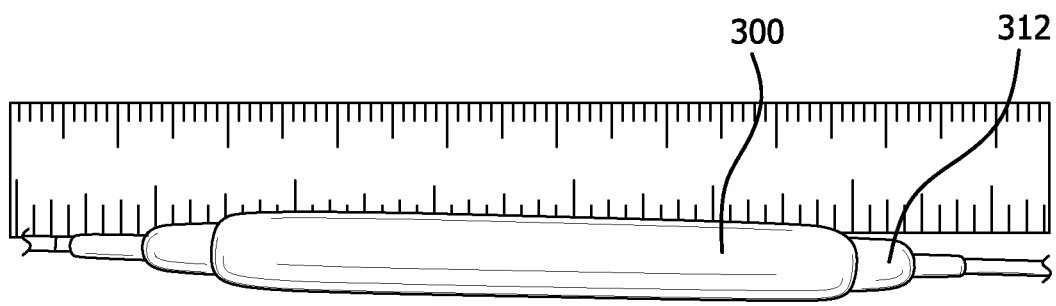
FIG. 3B  18 atm
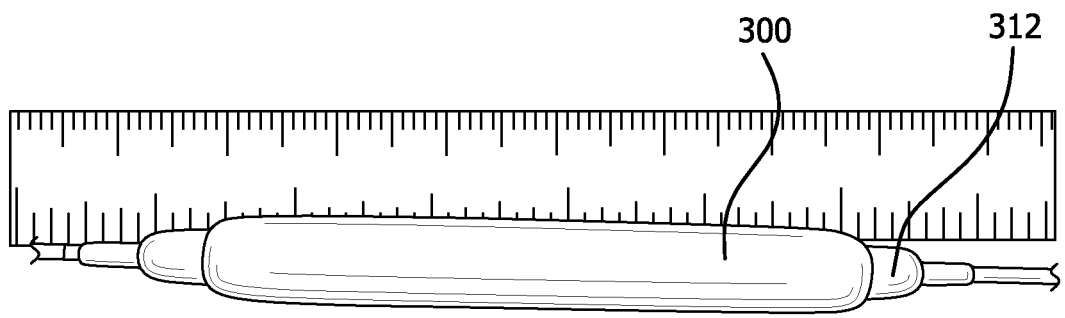
FIG. 3C  24 atm

BALLOON SEAL STRESS REDUCTION AND RELATED SYSTEMS AND METHODS

FIELD

The present disclosure generally relates to balloon seal stress reduction to reduce failure rates associated with balloon catheters.

BACKGROUND

Balloon catheters are often used in connection with medical treatments and deploying endoprosthetic devices. In a common scenario, a balloon secured to a catheter shaft with a seal is hydraulically inflated, and an overlying endoprosthetic device is thereby deployed from a smaller delivery diameter to a larger working diameter. In other instances, balloons used for medical treatments, for example percutaneous transluminal angioplasty (PTA) or localized drug delivery, require high balloon pressures on the order of 10-30 atmospheres. Robust balloon seals to prevent or mitigate unwanted failure of the balloon or reducing the stress on the seal can be beneficial, particularly for high pressure applications.

In addition, reducing the amount of stress on the balloon seal can also be beneficial, particularly for expandable balloons constructed from materials that will not retain a pre-formed or pre-molded shape upon inflation to a useable pressure range. These type of materials present an even greater challenge due to the geometry of the balloon shoulder regions upon inflation. Such balloons having distensible material(s) in the shoulder regions will tend to assume a shoulder wall geometry during inflation that does not taper in diameter between the working length and seal, e.g., the shoulders tend to be more vertical (square), near vertical, or sometimes assume an inverted state. This is in contrast to balloons made from generally non-distensible (e.g., non-compliant) especially pre-formed or molded, materials which, upon inflation, will produce a shoulder wall geometry which tapers from the end of the working length to the balloon seals, e.g., is conical. Shoulders which do not taper result in greater stress on adjacent balloon seals. Balloon seals where the balloons have more "square" rather than conical shoulders endure higher stresses at the seal. Balloons with such shoulder geometries could benefit from designs which reduce such seal stresses.

SUMMARY

Balloons of the present disclosure have shoulder portions with load sharing geometries, such as through the addition of a load sharing member.

In accordance with one aspect of the disclosure, a balloon can comprise a body portion inflatable to a first diameter and comprising a wrapped polymeric material; two seal portions, each having a second diameter smaller than the first diameter; and two shoulder portions, each defining a transition between the first diameter and the second diameter, wherein at least one shoulder portion comprises a load sharing member adapted to inhibit inflation beyond a diameter between the first diameter and the second diameter along at least a section of the shoulder portion. The body portion extending between the two shoulders, and the two shoulders and body portion extending between the two seal portions.

In accordance with another aspect of the invention, a balloon can comprise a body portion inflatable to a first diameter; two seal portions, each having a second diameter smaller than the first diameter; and two shoulder portions, each defining a transition between the first diameter and the second diameter, wherein at least one shoulder portion comprises a stepped geometry upon inflation of the balloon.

In accordance with another aspect of the invention, a method for reducing the hoop stress applied to a seal portion of on an expandable balloon having a body portion and two shoulder portions comprising the step of placing a load sharing member around a balloon along at least a portion of at least one of the two shoulder portions, wherein the balloon comprises a wrapped polymeric material.

The various aspects of the present disclosure can comprise a variety of additional or alternative features in any combination. In various embodiments, the wrapped polymeric material can comprise an expanded fluoropolymer, such as expanded polytetrafluoroethylene. In various embodiments, an outer edge of the body portion and an inner edge of the seal portion can be longitudinally offset from each other. In various embodiments, the load sharing member can comprise a structural reinforcement. In various embodiments, the load sharing member can extend along a substantial portion of the shoulder portion. In various embodiments, the shoulder portion can comprise a tapered geometry. In various embodiments, the load sharing member can comprise one of a conical frustum shaped structural reinforcement. In various embodiments, the load sharing member can comprise a material wrapped on conical shaped mandrel and optionally densified or imbibed. In various embodiments, the load sharing member can comprise a less distensible polymeric material molded into tapered shape. In various embodiments, the shoulder portion can comprise a stepped geometry. In various embodiments, the load sharing member can be isolated to an intermediate section of the shoulder portion. In various embodiments, the load sharing member can comprise a material that is a higher durometer than the wrapped polymeric material. In various embodiments, the load sharing member can comprise at least one of densified ePTFE or imbibed ePTFE. In various embodiments, the load sharing member can comprise a plurality of wraps of less distensible polymeric film. In various embodiments, the load sharing member can be located outside of the body portion of the balloon. In various embodiments, the load sharing member can comprise a pattern cut reinforcement, optionally nitinol.

BRIEF DESCRIPTION OF THE DRAWINGS

The accompanying drawings are included to provide a further understanding of the disclosure and are incorporated in and constitute a part of this specification, illustrate embodiments of the disclosure and together with the description serve to explain the principles of the disclosure.

FIG. 1 illustrates a cross-sectional view of a balloon catheter having squared shoulders;

FIG. 2A illustrates a cross-sectional view of a balloon catheter having a stepped shoulder geometry in accordance with the present disclosure;

FIG. 2B illustrates a cross-sectional view of a balloon catheter having a coned shoulder geometry in accordance with the present disclosure;

FIG. 2C illustrates a cross-sectional view of another balloon catheter having a stepped shoulder geometry in accordance with the present disclosure; and FIGS. 3A-3C illustrate an example of a balloon catheter in accordance with the present disclosure inflated to increasing pressures.

DETAILED DESCRIPTION

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

In general, the present disclosure is directed toward devices, systems and methods that reduce stress being exerted directly onto balloon seals.

With reference to FIG. 1, the present disclosure comprises a balloon 100. In general, balloon 100 comprises a collapsed configuration and an expanded configuration. In an expanded configuration, balloon 100 further comprises a shoulder portion 110 at each end of balloon 100. Shoulder portion 110 is that region where the diameter of balloon 100 circumferentially transitions between a larger diameter of a body portion or working length 120 of balloon 100 and a smaller diameter of a seal portion 130 of balloon 100. As shown in FIG. 1, these shoulder regions can assume a non-tapering, generally vertical, and/or square configuration upon inflation.

As illustrated, seal portion 130 generally operates to secure balloon 100 about a catheter 140 and provide a fluid tight interface between balloon 100 and catheter 140. Catheter 140 is typically provided with an inflation lumen and an outlet (not shown) for inflation of the balloon with an inflation media. In an embodiment, seal portion 130 comprises a reinforcement feature such as a plurality of wraps of a polymer film having a polymer and/or adhesive imbibed or deposited, on at least one surface of or at least partially into the film. For instance, the seal reinforcements can be formed using a plurality of wraps of an ePTFE film at least partially imbibed with cyanoacrylate imbibed.

Balloon 100 can further comprise a balloon cover surrounding a substantial portion of balloon 100. As used herein, reference made to a "balloon" shall be construed to also include a "balloon cover," as the geometries and structural configurations described below can be applied to a balloon cover in the same or a similar manner as a balloon.

Balloon 100 can comprise materials which are compliant to semi-compliant or materials that can be used to construct balloons with limited distensibility, e.g., wrapped polymeric materials. For example, balloon 100 can comprise one or more fluoropolymers like expanded polytetrafluoroethylene ("ePTFE"), expanded modified PTFE, expanded copolymers of PTFE, expanded polyethylene, and the like. In various embodiments, balloon 100 can comprise a helically, circumferentially, axially oriented balloon wall, such as by wrapping an ePTFE film to form balloon 100. As used herein, the term "axial" is interchangeable with the term "longitudinal." As used herein, "circumferential" means an angle that is substantially perpendicular to the longitudinal axis. As used herein, "helical" means an angle that is not parallel to the longitudinal axis and not substantially perpendicular. In various embodiments, to form a helically oriented balloon material, a film can be helically wrapped into a tubular form. Orientation can refer to the direction of a particular property, such as a strength or a microstructure feature, e.g., the fibrils.

Other materials with similar properties are within the scope of the present disclosure. For example, balloon 100 can be fabricated from a variety of commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenylene Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluoroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX). In addition, expandable balloons can be made from urethanes, silicones, fluoroelastomers, elastomers, and polyetherblockamides.

In accordance with the present disclosure, with reference to FIGS. 2A-2C, shoulder portion 110 of balloon 100 can comprise a load sharing geometry upon inflation. Further, shoulder portion 110 of balloon 100 can comprise one or more load sharing members that facilitate a load sharing geometry upon inflation.

A load sharing geometry is generally any inflated geometry of shoulder portion 110 of balloon 100 that reduces stress being exerted directly onto balloon seals. Without intending to be bound by theory, it is believed that hoop and end stress is directly proportional to the balloon diameter adjacent to the seal and can thus be lowered by a gradual (e.g., sloped or curved) or stepwise decrease to seal diameter from full diameter. In this regard, balloon 100 can comprise a longitudinal axis extending therethrough, wherein an outer edge 121 of body portion 120 and inner edge 131 of seal portion 130 are longitudinally offset or spaced apart. More specifically, and by way of non-limiting examples, a load sharing geometry can comprise a stepped geometry or a coned geometry.

For example, and with reference to FIGS. 2A and 2C, a stepped geometry can comprise one or more circumferential steps 112 at an intermediate diameter between a larger diameter of body portion 120 of balloon 100 and a smaller diameter of seal portion 130 of balloon 100. As illustrated, step 112 can comprise a circumferential ridge at a diameter less than the diameter of the body portion 120. The ridge can oriented substantially parallel to the longitudinal axis. The stepped balloon shoulder 110 can comprise at least two sections forming an angle of about 90 degrees adjacent the ridge, yet other angles greater than or less than 90 degrees are within the scope of the present disclosure.

With reference to FIG. 2B, a coned or tapered geometry can comprise a circumferential taper 114 between a larger diameter of body portion 120 of balloon 100 and a smaller diameter of seal portion 130 of balloon 100. As illustrated, taper 114 can form an angle between about 35 to 65 degrees angle, yet other angles greater than or less than the stated range are within the scope of the present disclosure.

Other geometries are within the scope of the present disclosure as well, for example, one that comprises a curve transition between the larger diameter of body portion 120 of balloon 100 and the smaller diameter of seal portion 130 of balloon 100.

In various embodiments, a load sharing geometry is imparted to a shoulder of a balloon by one or more load sharing members. At least a portion of a load sharing member is less distensible than the body portion. Less distensible load sharing member can comprise a material of a higher durometer or stiffness than the material of the body portion, a material and/or construct that is less distensible than the material or construct of the body portion, a material or construct that is non-distensible, or any material or construct that inhibits distension of the shoulder portion beyond an intermediate diameter, i.e., a diameter between the larger diameter of the body portion of a balloon and the smaller diameter of the seal of the balloon. In various embodiments, a load sharing member is outside of the body portion or working length of the balloon, e.g., the portion which is intended to contact the luminal surface of an endoprosthetic device and/or surrounding tissue, and away from or extending only along the shoulder portion toward the seals of a balloon.

In some embodiments, a load sharing member facilitates a load sharing geometry but does not extend along a substantial portion of shoulder 110; e.g., the load sharing member is isolated to an intermediate portion of the shoulder. By way of non-limiting example, and with reference back to FIG. 2A, a load sharing member can comprise a band 113 that facilitates circumferential step 112 and imparts a stepped shoulder geometry. In other embodiments, a load sharing member substantially extends along a substantial portion of shoulder 110. For example, and with reference to FIG. 2B, a load sharing member can comprise a conical frustum 115 that extends along a substantial portion of shoulder 110 to form a coned or tapered shoulder geometry. Other geometries are within the scope of the present disclosure as well.

With reference to FIG. 2C, in other embodiments, shoulder portion 110 can comprise multiple load sharing members, such as, for example more than one band 113.

In some embodiments, a load sharing member is a region (e.g., a band or conical frustum region) of a balloon where the balloon material is modified. One such modification comprises densifying the balloon material, for example ePTFE, along a target region of the shoulder. Such densification can be graded to create a tapered load sharing geometry. In various embodiments, densifying can be accomplished by applying pressure and/or localized heat to a target region of the balloon material (e.g., by sintering, lasering, lasering in a pattern, etc.).

Another such modification comprises coating or imbibing a target region of a balloon shoulder with a generally less distensible or non-distensible material (e.g., fluorinated ethylene propylene (FEP), PATT, a thermoplastic, nylon, and the like). For example, in illustrative embodiments comprising an ePTFE balloon material, imbibing involves at least partially filling the pores of the porous ePTFE with the generally less distensible polymeric material at the target region.

In various embodiments, the shoulder portion can comprise or consist essentially of a second material having a durometer that is higher than that of the body portion of the balloon. In other words, the material of the body portion would not be continuous from the body portion along the shoulder portion to the seal but is interrupted by the second material in at least a portion of the shoulder portion.

In various embodiments, a load sharing member can be a structural reinforcement (e.g., having a band or conical frustum geometry) that has been added to a region of a balloon. Such a structural reinforcement can be situated between layers of a balloon, between a balloon and a balloon cover, on the surface of a balloon, and/or under the balloon wall. Such a structural reinforcement can be adhered (such as through use of a heat treatment and/or adhesive) to the balloon/balloon cover or otherwise fixed in position. In accordance with an aspect of such embodiments, a structural reinforcement can comprise a wrapped member, a molded member, a woven or knitted member, a die cut or laser cut member, or any other appropriately shaped reinforcement construct.

For example, a structural reinforcement can comprise a material that has been wrapped on an appropriately shaped mandrel and densified or imbibed as described above.

For example, a structural reinforcement can comprise a polymeric material of higher durometer than the body portion that is molded (e.g., blown or extruded) into an appropriate shape.

For example, a structural reinforcement comprises a pattern cut reinforcement or similar structure. The pattern cut reinforcement can comprise nitinol or other similar shape memory material. For example, a nitinol reinforcement can comprise a collapsible annular member like a stent ring to facilitate a stepped geometry. Alternatively, a nitinol reinforcement can comprise a conical frustum geometry in an expanded configuration, e.g., an annular base, which can be collocated with the seal, having a plurality of nitinol struts that extend from the band and are adapted to form a conical frustum load sharing geometry upon inflation of the balloon.

Thus, in accordance with the present disclosure, a load sharing geometry reduces stress being exerted directly onto balloon seals and thereby reduces failure rates associated with balloon catheters.

Example of making an ePTFE wrapped balloon cover comprising a stepped load sharing geometry:

A stepped balloon can be manufactured as follows. An ePTFE balloon cover (e.g., a cover comprising a wrapped ePTFE film) can be mounted on a mandrel at a first diameter (e.g., 8 millimeters) and necked or reduced in diameter to a necked portion having a necked diameter of approximately 0.070 inches (1.778 millimeters). The cover can then be expanded to approximately 4 millimeters and placed over a similarly sized mandrel. An anisotropic ePTFE film strip (approximately 5 mm wide) coated with a thermoplastic copolymer of tetrafluoroethylene and perfluoroalkylvinylether (as described in U.S. Pat. No. 7,462,675 to Chang et al., which is incorporated by reference herein in its entirety) can then be wrapped around the cover about the sections of the cover to be part of the shoulder portion. The film can be wrapped at least two times so that the stronger direction of the film strip will oriented around the circumference of the balloon. The ePTFE film strip can be a dense, strong ePTFE that is 2-6 µm thick made generally in accordance with the teachings of U.S. Pat. No. 7,521,010 to Kennedy, which is incorporated herein by reference in its entirety. The thickness of the copolymer coating can range from 1-3 µm. The section of the cover having the 5 mm ePTFE film strip wrapping can be thermally treated after wrapping to cause the layers to adhere to each other and to the cover. The cover can then be placed over a balloon and secured to the catheter at each end.

The covered balloon can be inserted into a tube of material configured to shrink or contract at a particular temperature (e.g., an FEP shrink tube), and the covered balloon, once in position, can be heated at approximately 260 degrees Celsius. The covered balloon can be further reduced in diameter, or sized down from a 4 mm intermediate diameter, to approximately 0.100 inches (2.5 millimeters) using a radial crusher.

Thus, as described, a balloon can be manufactured to a stepped, load sharing geometry. FIGS. 3A-3C show such a covered balloon 300 inflated to increasing pressures, from 14 to 24 atmospheres. As can be seen, at lower pressures, the difference between the diameter of the balloon at body portion 120 and the diameter at circumferential step 312 is less than at greater pressures, but circumferential step 312 is non-distensible beyond an intermediate diameter even as the body of balloon 300 increases in diameter under increasing pressures.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A balloon comprising:
    a body portion inflatable to a first diameter and comprising a wrapped polymeric material, the wrapped polymeric material comprising expanded polytetrafluoroethylene (ePTFE);
    two seal portions that extend horizontally, each having a second diameter smaller than the first diameter; and
    two shoulder portions, each of the two shoulder portions has an intermediate diameter that transitions from the first diameter of the body portion to the second diameter of the two seal portions, one of the two shoulder portions positioned between an outer edge of the body portion and a longitudinally offset inner edge of one of the two seal portions and the other of the two shoulder portions positioned between another outer edge of the body portion and a longitudinally offset inner edge of the other of the two seal portions,
    wherein at least one of the two shoulder portions comprises a load sharing member that imparts a load sharing geometry to the at least one of the two shoulder portions, wherein the load sharing member extends only along the at least one shoulder portion towards at least one of the two seal portions and not over the body portion,
    wherein at least a portion of the load sharing member comprises a material that is less distensible than the ePTFE of the body portion, and the material inhibits distension of the at least one of the two shoulder portions beyond the intermediate diameter between the first diameter and the second diameter to reduce stress on the at least one of the two seal portions, and
    wherein the at least one of the two shoulder portions comprises a stepped geometry to form a single circumferential step at the intermediate diameter defined by a first shoulder section that extends horizontally and a second shoulder section that extends vertically such that the shoulder sections are perpendicular to each other.

2. The balloon of claim 1, wherein the load sharing member comprises a structural reinforcement.

3. The balloon of claim 1, wherein the load sharing member extends along a substantial portion of the at least one of the two shoulder portions.

4. The balloon of claim 1, wherein the load sharing member is isolated to an intermediate section of the at least one of the two shoulder portions.

5. The balloon of claim 1, wherein the material that is a higher durometer than the wrapped polymeric material of the body portion.

6. The balloon of claim 1 wherein the material comprises at least one of densified ePTFE or imbibed ePTFE.

7. The balloon of claim 1, wherein the material comprises a nitinol reinforcement.

8. The balloon of claim 1 wherein the wrapped polymeric material extends beyond the body portion of the balloon to form the two shoulder portions, and further wherein the load sharing member is defined by a region of the wrapped polymeric material that is densified.

9. A balloon comprising: a body portion inflatable to a first diameter comprising a wrapped polymeric material comprising ePTFE;
    two seal portions, each having a second diameter smaller than the first diameter; and
    two shoulder portions, each of the two shoulder portions has an intermediate diameter that transitions from the first diameter of the body portion to the second diameter of the two seal portions, one of the two shoulder portions positioned between an outer edge of the body portion and a longitudinally offset inner edge of one of the two seal portions and the other of the two shoulder portions positioned between another outer edge of the body portion and a longitudinally offset inner edge of the other of the two seal portions,
    wherein at least one of the two shoulder portions includes a load sharing member that is isolated to the at least one of the two shoulder portions and does not extend over the body portion,
    wherein at least a portion of the load sharing member comprises a material that is less distensible than the ePTFE of the body portion, and the material inhibits distension of the at least one of the two shoulder portions beyond the intermediate diameter between the first diameter and the second diameter to reduce stress on at least one of the two seal portions, and wherein the at least one of the two shoulder portions comprises a stepped geometry upon inflation of the balloon to form a single circumferential step at the intermediate diameter wherein the shoulder portions define a first shoulder section that extends horizontally and a second shoulder section that extends vertically such that the shoulder sections are perpendicular to each other.

10. The balloon of claim 9, wherein the load sharing member comprises a structural reinforcement.

11. The balloon of claim 9, wherein the material a higher durometer than the body portion.

12. The balloon of claim 9, wherein the load sharing member is isolated to an intermediate section of the at least one of the two shoulder portions.

13. The balloon of claim 9, wherein the load sharing member comprises at least one of densified ePTFE or imbibed ePTFE.

14. The balloon of claim 9, wherein the load sharing member is located outside of the body portion of the balloon.

15. The balloon of claim 9, wherein the load sharing member comprises a nitinol reinforcement.

16. The balloon of claim 9 wherein the wrapped polymeric material extends beyond the body portion of the balloon to form the two shoulder portions, and further wherein the load sharing member is defined by a region of the wrapped polymeric material that is densified.

17. A balloon comprising:
a body portion inflatable to a first diameter and comprising a wrapped polymeric material, the wrapped polymeric material comprising expanded polytetrafluoroethylene (ePTFE);

two seal portions that extend horizontally, each of the two sealed portions having a second diameter smaller than the first diameter; and two shoulder portions, each of the two shoulder portions has an intermediate diameter that transitions from the first diameter of the body portion to the second diameter of the two seal portions, one of the two shoulder portions positioned between an outer edge of the body portion and a longitudinally offset inner edge of one of the two seal portions and the other of the two shoulder portions positioned between another outer edge of the body portion and a longitudinally offset inner edge of the other of the two seal portions, wherein at least one of the two shoulder portions comprises at least one load sharing member that each imparts a load sharing geometry to the at least one of the two shoulder portions, wherein the load sharing member is isolated to the at least one of the two shoulder portions portion and extends only along the at least one of the two shoulder portions towards one of the two seal portions, wherein at least a portion of the load sharing member comprises a material that is less distensible than the ePTFE of the body portion, and the material inhibits distension of the at least one of the two shoulder portions beyond the intermediate diameter between the first diameter and the second diameter to reduce stress on the at least one of the two seal portions, and wherein the at least one of the two shoulder portions comprises a stepped geometry to form a single circumferential step at the intermediate diameter defined by a first shoulder section that extends horizontally and a second shoulder section that extends vertically such that the shoulder sections are perpendicular to each other.

* * * * *